United States Patent
O'Brien et al.

(10) Patent No.: US 10,773,103 B2
(45) Date of Patent: Sep. 15, 2020

(54) REALTIME RADIOTHERAPY MARKERLESS CALIBRATION AND MEASUREMENT SYSTEM

(71) Applicant: RESPIRATORY INNOVATIONS PTY LTD, Eveleigh, New South Wales (AU)

(72) Inventors: Ricky O'Brien, Five Dock (AU); Kuldeep Makhija, Blacktown (AU); Daniel Nicholas Zafir, Newtown (AU); Thomas Christopher Wolfgang Landgrebe, Sydney (AU); Peter Horsley, Wahroonga (AU); Sean Pollock, Redfern (AU); Paul J. Keall, Greenwich (AU)

(73) Assignee: Opus Medical Pty Ltd, Eveleigh, NSW ( * ) Notice: Subject to any disclaimer, the term of this patent is extended or adjusted under 35 U.S.C. 154(b) by 144 days.

(21) Appl. No.: 16/315,711

(22) PCT Filed: Jul. 6, 2017

(86) PCT No.: PCT/EP2017/066926
§ 371 (c)(1),
(2) Date: Jan. 7, 2019

(87) PCT Pub. No.: WO2018/007518
PCT Pub. Date: Jan. 11, 2018

(65) Prior Publication Data
US 2019/0209871 A1    Jul. 11, 2019

Related U.S. Application Data (60) Provisional application No. 62/358,712, filed on Jul. 6, 2016.

(51) Int. Cl.
*A61N 5/10*    (2006.01)
*G06T 7/73*    (2017.01)
(Continued)

(52) U.S. Cl.
CPC .............. *A61N 5/1075* (2013.01); *A61B 6/04* (2013.01); *A61N 5/1037* (2013.01);
(Continued)

(58) Field of Classification Search
CPC ...... A61N 5/10; A61N 5/1037; A61N 5/1049; A61N 5/1075; A61B 6/04
(Continued)

(56) References Cited

U.S. PATENT DOCUMENTS

2006/0079757 A1    4/2006  Smith et al.
2016/0129283 A1    5/2016  Meir et al.

FOREIGN PATENT DOCUMENTS

GB          2532077 A     11/2014
WO    WO-2016015760 A1 *  2/2016  ............. G06T 7/521

\* cited by examiner

*Primary Examiner* — John P Lacyk
(74) *Attorney, Agent, or Firm* — Lumen Patent Firm (57) ABSTRACT

A method of real-time markerless measurement and calibration of a patient positioning system includes computing a three dimensional point cloud representation of a patient by using a camera to obtain depth points of the patient, where the z-direction corresponds to a direction along the focal length of the camera, demanding a z-limit that corresponds to a lower (z-min) and an upper (z-max) specification, computing a point cloud covariance and a point cloud mean for an optimized principle components analysis to compute a torso topography of the patient, determining a center point of the point cloud as an anchor measurement region and using the camera to determine a distance to the patient to establish an angle between a patient torso and a vector that is perpendicular to the camera, averaging the depth measurements in reference regions and compensating for parallax error in real-time during a calibration measurement or radiotherapy treatment plan.

4 Claims, 11 Drawing Sheets

(51) Int. Cl.
*G16H 30/20* (2018.01)
*G16H 50/50* (2018.01)
*G06T 7/579* (2017.01)
*G06T 7/80* (2017.01)
*A61B 6/04* (2006.01)

(52) U.S. Cl.
CPC ............ *A61N 5/1049* (2013.01); *G06T 7/579* (2017.01); *G06T 7/73* (2017.01); *G06T 7/85* (2017.01); *G16H 30/20* (2018.01); *G16H 50/50* (2018.01); *A61N 2005/105* (2013.01); *A61N 2005/1059* (2013.01); *G06T 2207/10028* (2013.01); *G06T 2207/30004* (2013.01)

(58) Field of Classification Search
USPC .......................................................... 600/1–8
See application file for complete search history.

Person in position
FIG. 1A

Depth map with torso vectors and measurement zones annotated
FIG. 1B

REALTIME RADIOTHERAPY MARKERLESS CALIBRATION AND MEASUREMENT SYSTEM

CROSS-REFERENCE TO RELATED APPLICATIONS

This application is a 371 of PCT application PCT/EP2017/066926 filed on Jul. 6, 2017. PCT application PCT/EP2017/066926 claims the benefit of U.S. Provisional application 62/358,712 filed on Jul. 6, 2016.

FIELD OF THE INVENTION

The present invention relates generally to radiotherapy and medical imaging procedures. More particularly, the invention relates to markerless calibration and measurement for patient breathing in radiotherapy treatment and medical imaging procedures.

BACKGROUND OF THE INVENTION

With radiotherapy, there is a need to position the patient in the same position, when obtaining diagnostic images and each of the subsequent times when radiation is applied to the patient's body. Present systems for positioning patients include various forms of systems for placing markers on the patient to enable the patient to be realigned for different applications of therapy. These systems are problematic in terms of aspects such as repeatability.

What is needed is a markerless calibration and measurement system that does not rely on marker placement on the patient to automatically determine breathing measurement regions.

SUMMARY OF THE INVENTION

To address the needs in the art, a method of real-time markerless measurement and calibration of a patient positioning system (PCA) is provided that includes computing a three dimensional point cloud representation of a patient by using a camera to obtaining a plurality of depth points (X, Y, z) of the patient, where the camera includes pixel coordinates (x, y) and depth to target z, where the X-direction corresponds to a lateral dimension of the patient, where the Y-direction corresponds to a longitudinal direction of the patient, where the z-direction corresponds to a direction along the focal length of the camera, where for each (x, y) and (X, Y, z) a corresponding point cloud coordinate xp, yp, z is determined as a function of the camera focal length, camera sensor center position, pixel size and lens distortion parameters. Then demanding a z-limit on the z-direction that corresponds to a lower (z-min) and an upper (z-max) specification, computing a point cloud covariance and a point cloud mean, where the covariance and the mean of the point cloud are used to perform an optimized principle components analysis, where the principle components are determined, sorting the principle components according to their maximum eigen-values, where the sorted principle components are used to compute a torso topography of the patient, determining a center point of the point cloud, where the center point is used as an anchor measurement region of the patient, where a plurality of other measurement regions are determined along the Y-direction of the patient, where an eigen-vector of least variance along the z-direction is determined from all the measurement regions, where the least variance eigen-vector is perpendicular to the patient, using the camera to determine a distance to the patient along the least variance eigen-vector in real-time, and outputting a real-time patient torso position, where the least variance eigen-vector of the anchor measurement region establishes an angle between a patient torso and a vector that is perpendicular to the camera, where a difference in displacement of the patient torso is computed by averaging the depth measurements in the reference regions and compensating for a parallax error in real-time during a calibration measurement or during a radiotherapy treatment plan.

According to one aspect of the invention, after demanding the z-limit a torso fitter is applied, where the torso fitter comprises removing non-torso data of the patient. In one aspect here, after applying the torso fitter, physiological constraints are applied to the patient, where the constraints and the measurement regions are used to remove data outside a threshold that is vertically below a surface of the patient, where a filtered point cloud is provided. In a further aspect here, after applying the body metric constraints, the filtered point cloud is passed into a mesh resampling algorithm, where the mesh resampling algorithm demands an enhanced uniformity of a data sampling distribution across the torso of the patient, where the resampling algorithm reduces data samples on the patient that are proximal to the camera and increases data samples on the patient that are distal to the patient, where an enhanced data uniformity is provided, where regions without data are excluded, where the enhanced data uniformity is used to compute the patient torso orientation by applying the torso fitter to the point cloud then uniformly resampling the mesh and repeating the real-time markerless measurement and calibration of a patient positioning process, where the uniform resampling makes sure the PCA is not biased towards a part of the patient torso that is proximal to the camera.

DETAILED DESCRIPTION

The current invention provides a system and method of markerless calibration and measurement for radiotherapy treatment. According to one aspect, the invention includes a C #/C++ application with a user interface, camera sensor integration, patient interaction and logging. The markerless calibration system includes a real-time point-cloud processing software module for automatically determining measurement locations along the torso of a patient as per sensor setup guidelines. Two exemplary algorithmic workflows are provided that automatically determine breathing measurement regions, given a depth sensor positioned as per patient body and sensor specifications. The method is able to robustly identify suitable locations, with substantial invariance to the position of the person and sensor, and insensitivity to movements and clutter.

According to the current invention, the basis for the markerless measurement and calibration lies in utilizing known information about the shape of the torso, rough orientation of the target person relative to the sensor, and coarse geometric constraints. Importantly, the depth information together with intrinsic camera sensor information, such as focal lengths and center point, provide a reliable 3-dimensional sampling of the person and surroundings. In FIGS. 1A-1D the 3D method inputs and outputs are summarized, illustrating how a computed 3-dimensional point cloud forms the basis for both identifying an "anchor" position on the chest, and for establishing target measurement regions. A depth camera (sensor) is used to return the z-distance to patient directly.

The current invention includes the implementation of two method workflows, referred to as "PCA" and "PCA+Fitter", respectively, where the latter is an extension of the former.

Figure 1A:
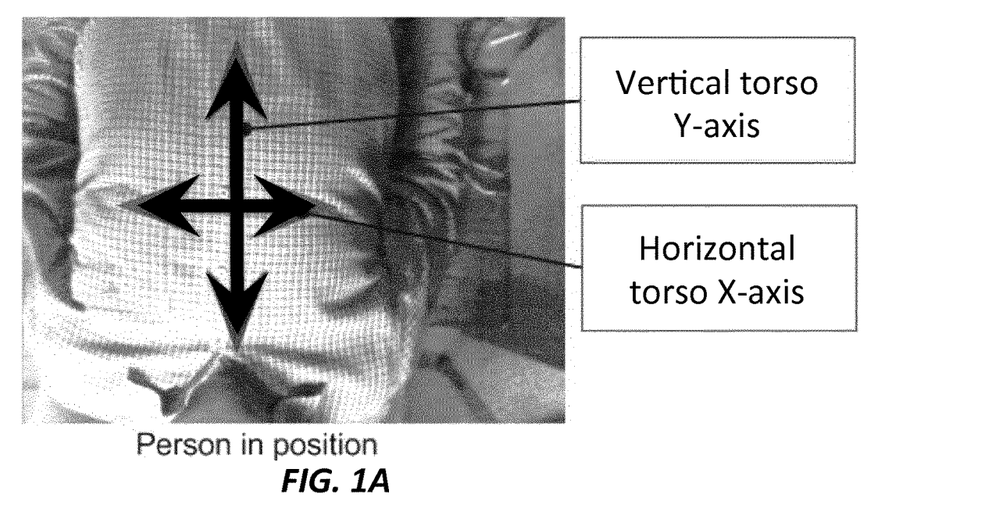
FIGS. 1A-1D. show (1A-1C) the core markerless calibration algorithm analysis, i.e. a point-cloud processing workflow to compute the location and orientation of the chest, and to automatically place target breathing measurement regions down the vertical axis of the torso, (1D) the orientation of the torso relative to the camera is also necessary to compensate for the parallax depth measurement error due to camera angle during the measurement process, according to the current invention.
Figure 1B:
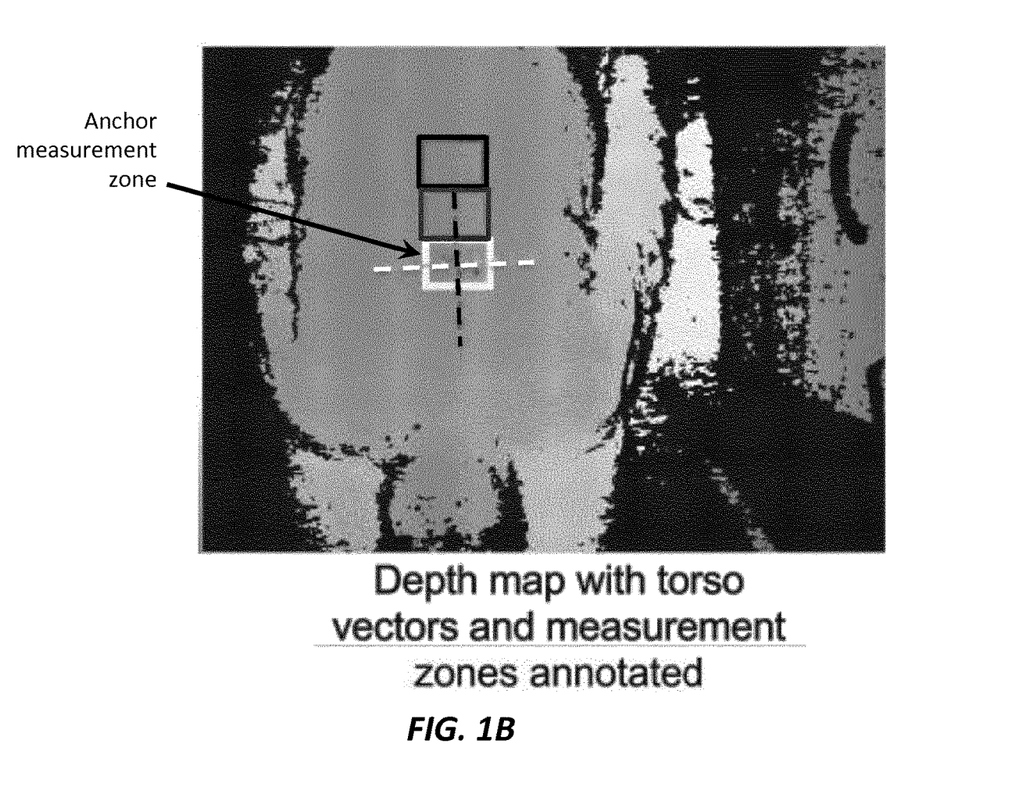
Figure 1C:
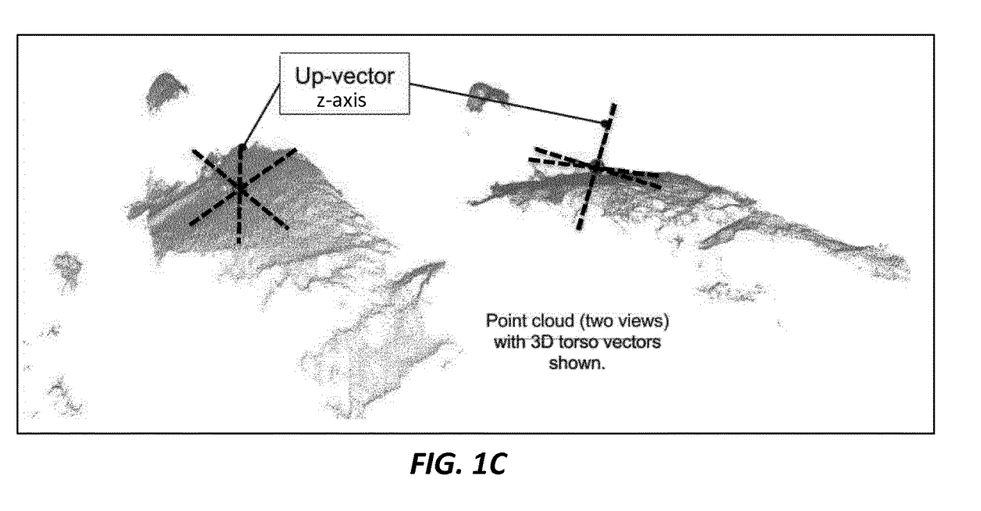
Figure 1D:
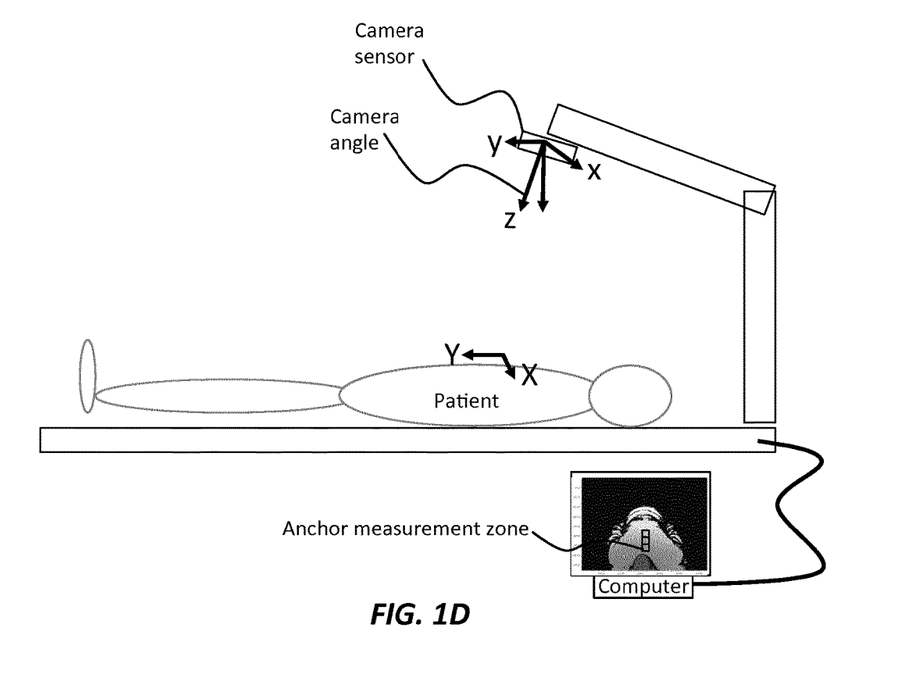
Figure 2:
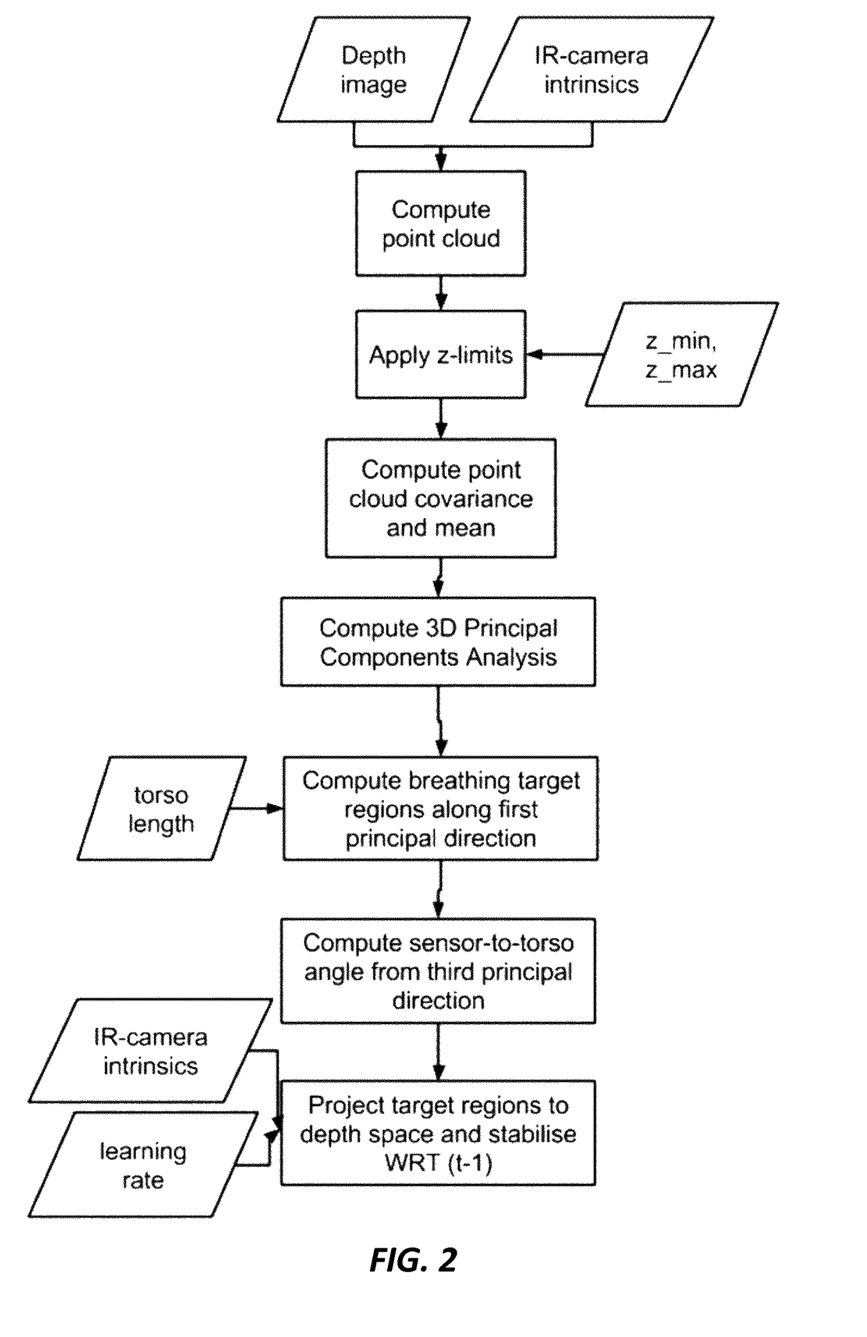
FIG. 2 shows a markerless dynamic calibration algorithm1 workflow, according to the current invention.

Turning now to the PCA method, which establishes the following workflow, as summarized in FIG. 2. Here, the original depth image is converted to a point cloud, using calibration parameters to project pixels in (x, y) to meters, where the point cloud is cropped in the z-direction to eliminate unreliable readings at the extremities. Next, an optimized principal-components analysis is performed on the point cloud, where, to save time, the analysis explicitly uses the fact that the covariance is symmetrical. The resultant principal-components are sorted via the maximum eigen-values, and used to compute the torso calculations. The first component is the direction of the point cloud in which there is maximal variance, which tends to be the vertical direction of the data for appropriate sensor-to-body configurations. The center of the point cloud is used to establish an "anchor" measurement region, where additional measurement regions are established down the direction of the main component according to the length of the torso (specified). This places the target measurement regions along key locations on the torso, allowing the most appropriate one to be selected for the breathing measurements. The orientation of the third eigen-vector is a very stable direction in the data, that is, the direction in which there is the least variance, which corresponds to the vector that is perpendicular to the torso. The advantage of this method is that it is fast, numerically stable, and adjusts to the orientation of the body.

This aspect of the method is more sensitive to clutter in the field of view, e.g. objects or people next to the bed. These can affect the principal directions of the data. Further, when the 3D sensor (or IR sensor) is very close to the torso, the projected infrared grid pattern is strongly biased towards parts of the torso close to the sensor (see FIG. 4A), whereas further away the sampling becomes very sparse. This has a strong influence on the calculation of the principal directions, with the solution being to maintain a minimum distance from the torso, where the dynamic range of the sensor is not exploited, and the method has less flexibility. Here, the second workflow, referred to here as the PCA-fitter method, is provided to improve upon these issues, and to make better use of geometric constraints that are available.

Figure 3:
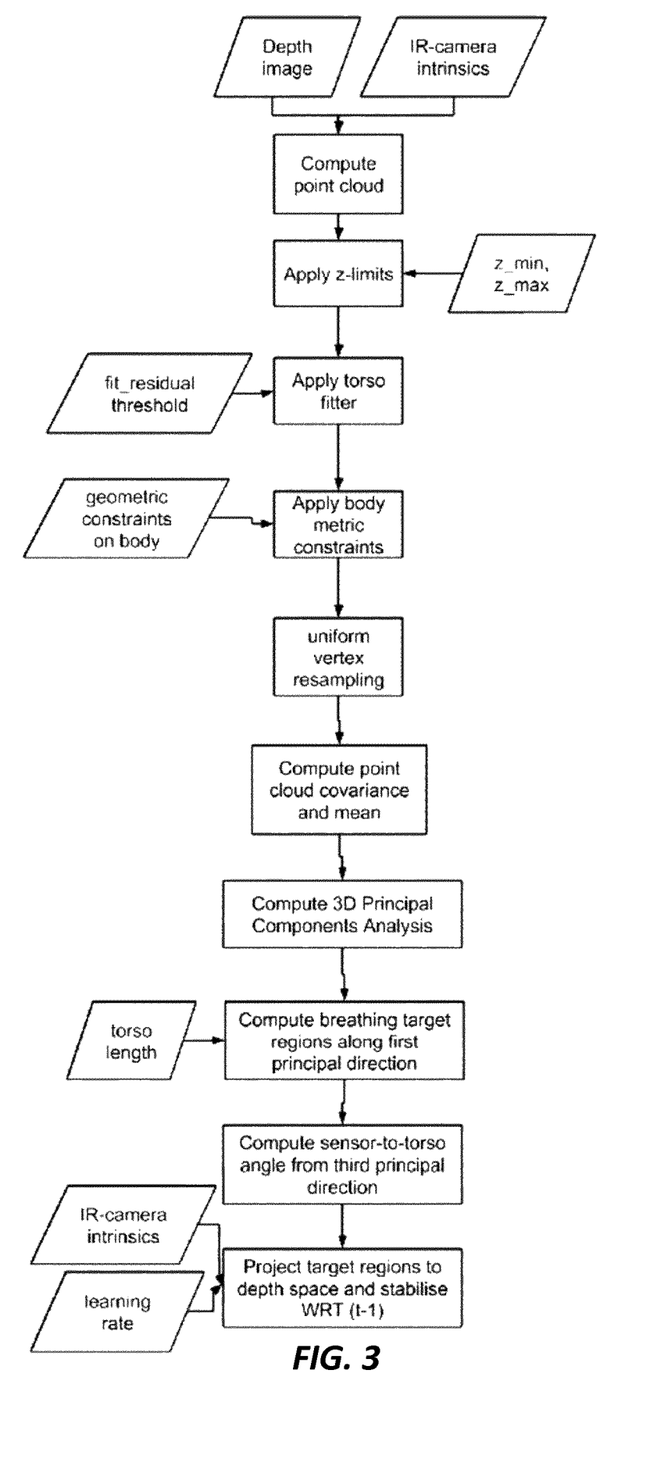
FIG. 3 shows markerless dynamic calibration algorithm2 workflow, according to the current invention.

Turning now to the PCA-fitter method, where this second workflow makes use of the same workflow as the first, but with a number of additional processing steps inserted after the point cloud computation as shown in FIG. 3. Note that this does not imply the method is slower, since the new steps reduce the amount of processing required in later steps. After the point cloud computation (PCA method), the following additional processes are implemented for the second aspect of the method. A torso fitter has been established, which comprises a curved 3-dimensional surface, making use of the fact that the torso is laterally curved. As such, the mathematical function uses a second order quadratic in the lateral (across chest) direction, and a linear model down the vertical of the torso (4 parameters in total). Note that the approach has been designed to be very insensitive to clothing and body shape differences, and is instead focused on eliminating clutter confidently distant from the fitted model. The RANSAC optimization methodology has been used in order to achieve computational requirements and robustness to outliers. Since the torso dominates the view, the number of RANSAC iterations can be kept small, where the probability of randomly drawing 4 samples that lie on the surface is high. The torso fitter includes all data within a residual threshold. Knowledge of the approximate body size constraints and required viewing regions is explicitly used to remove data outside a threshold vertically below the torso. It was also found that removing data symmetrically along the vertical axis of the torso (i.e. horizontal removal) enforces a filtered point cloud that is elongated vertically, which subsequently results in a very accurate principal direction finding in the final stage. This is especially useful for sensor setups that are close to the body, or for imaging people that are significantly larger than average. The filtered point cloud is passed into a mesh resampling algorithm to produce a uniformly sampled point cloud, as illustrated in FIG. 4B (under-sampled for illustrative purposes). This was a subtle but essential step for the markerless methodology, especially where the sensor is in close proximity to the torso. In this scenario the infrared projector produces a highly biased sampling of the torso i.e. more points sampled on the upper torso, which results in poor extraction of the principal directions. A computationally efficient approach was implemented by creating a grid pattern using the coefficients of the fitted surface. The final filtered and resampled point cloud is then passed on to the body-vector analysis.

Figure 5A:
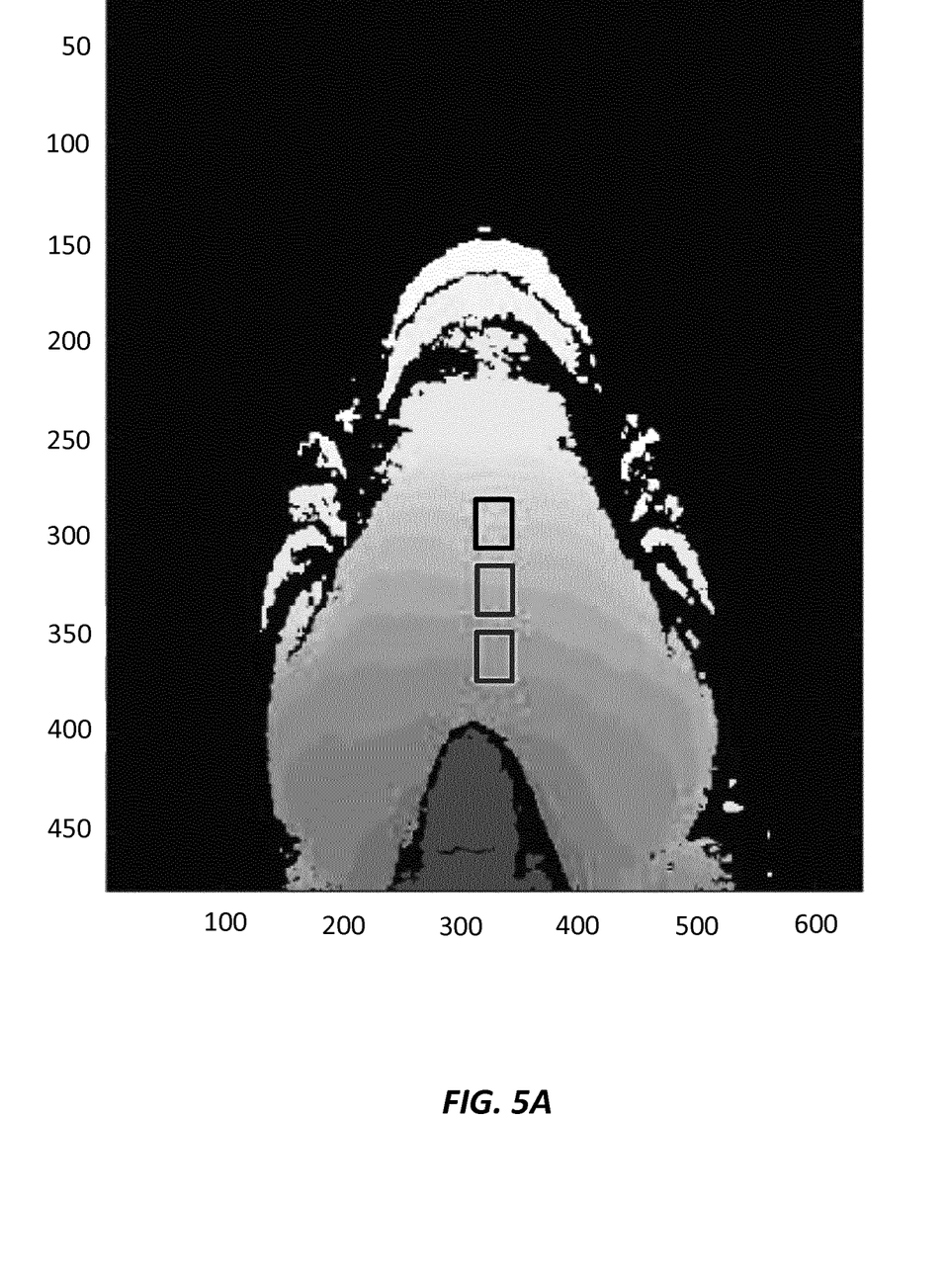
FIGS. 5A-5C show the measurement algorithm extracting breathing waveforms in three target regions. The angle between the sensor and torso is used to correct the parallax error between the viewing angle and the breathing displacement (compare raw measurements in 5B to corrected measurements in 5C), according to the current invention.
Figure 5B:
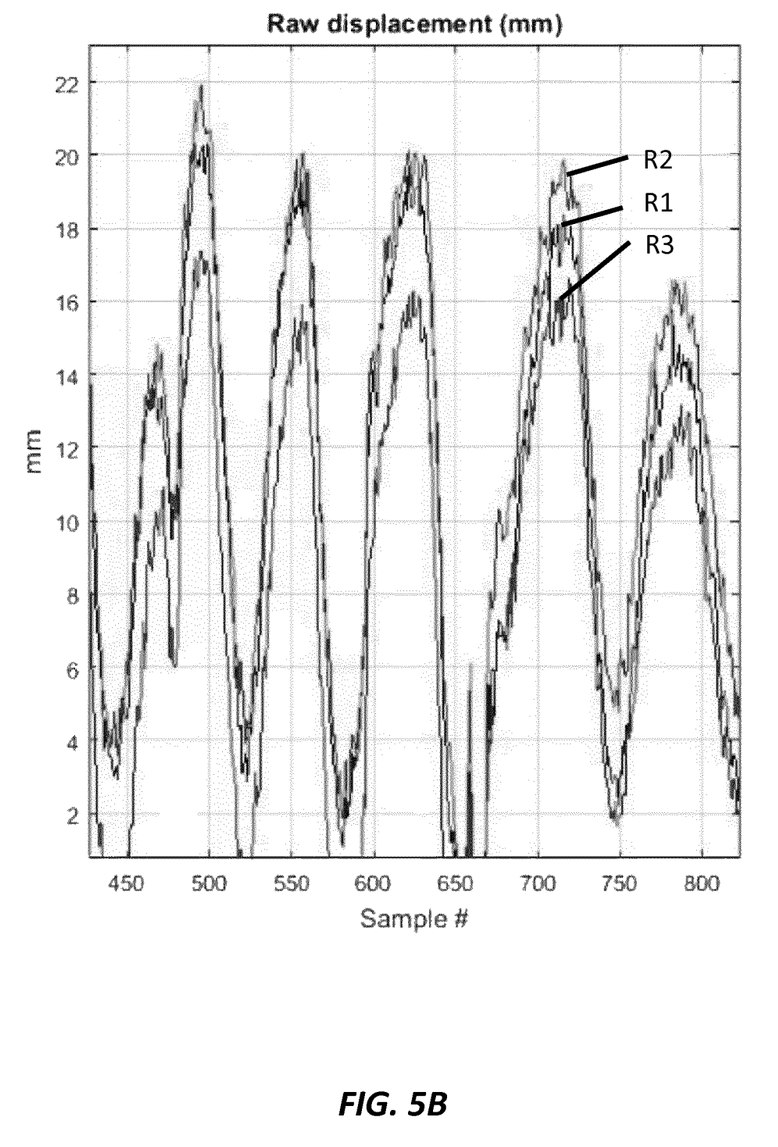
Figure 5C:
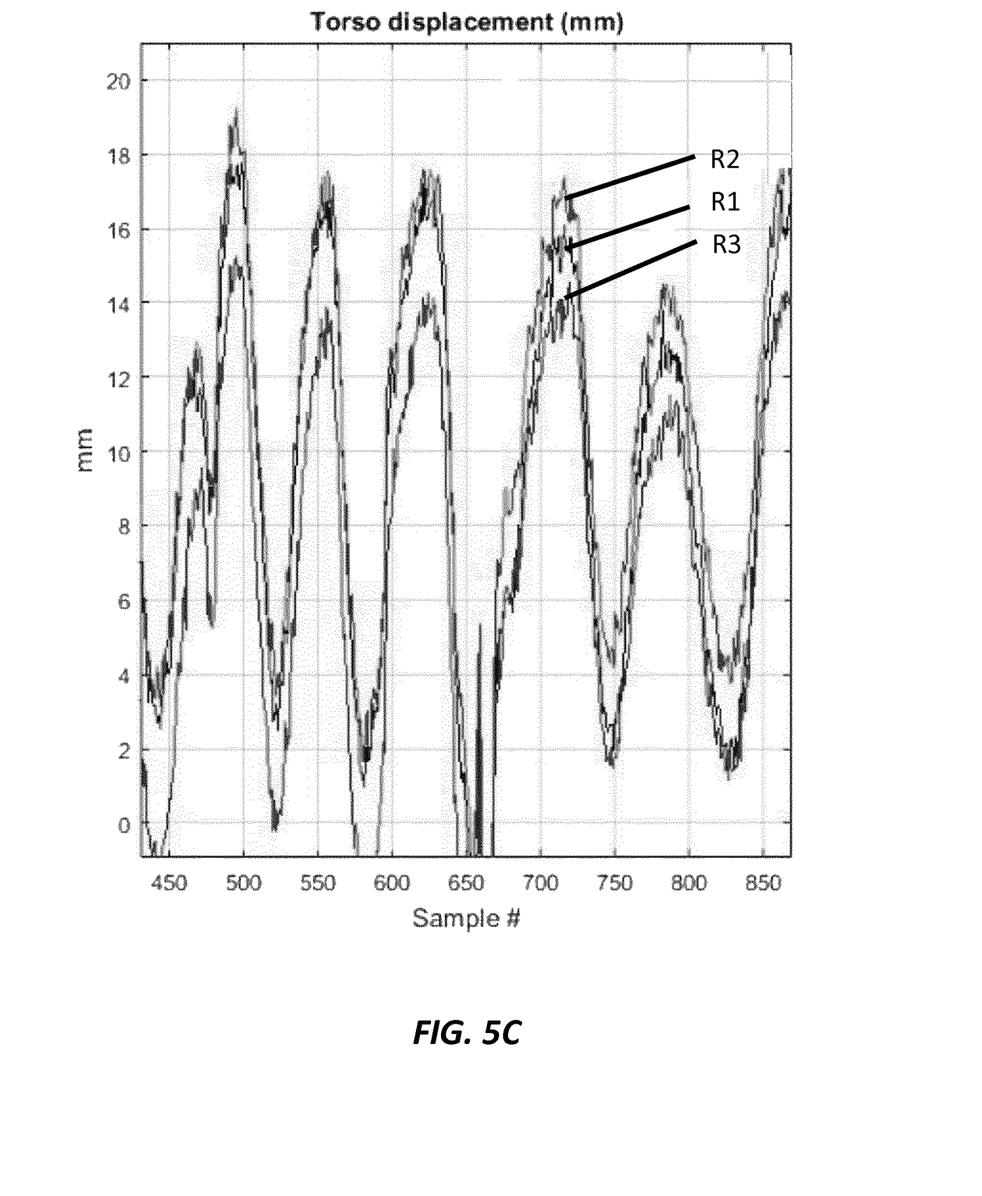
Figure 6A:
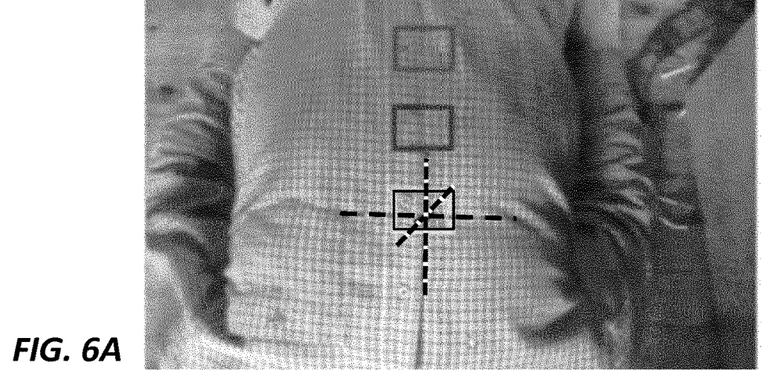
FIGS. 6A-6I show images that highlight the output of the markerless calibration system in a variety of situations, according to the current invention.
Figure 6B:
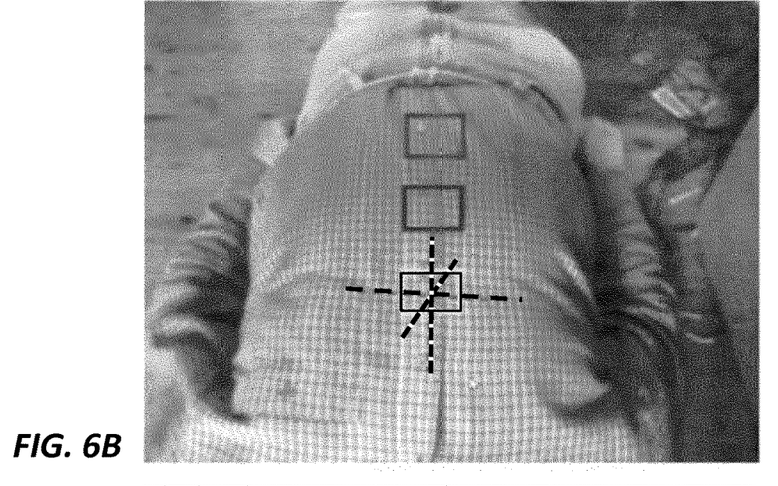
Figure 6C:
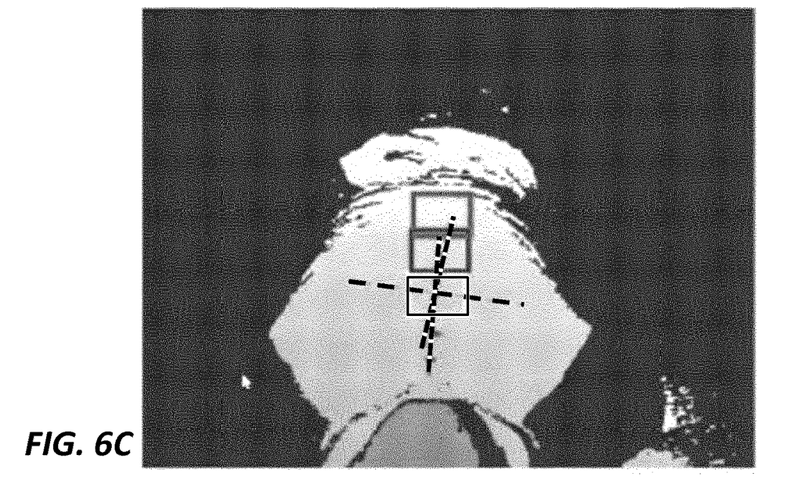
Figure 6D:
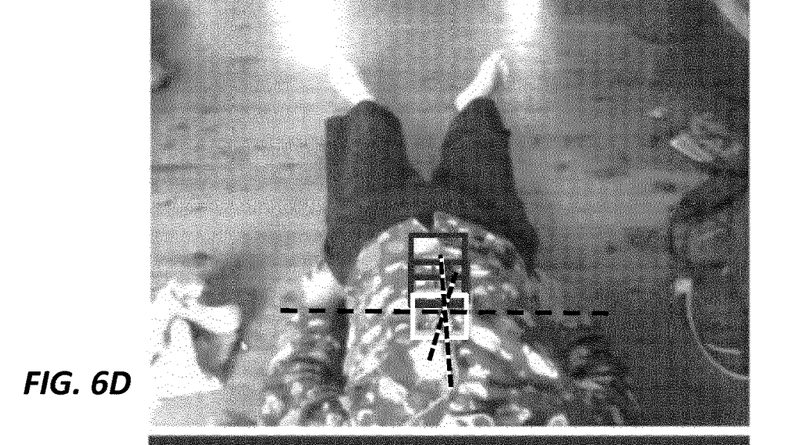
Figure 6E:
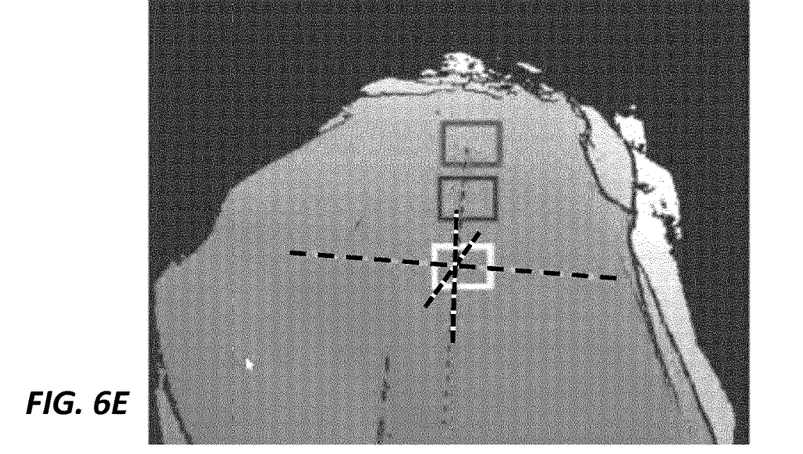
Figure 6F:
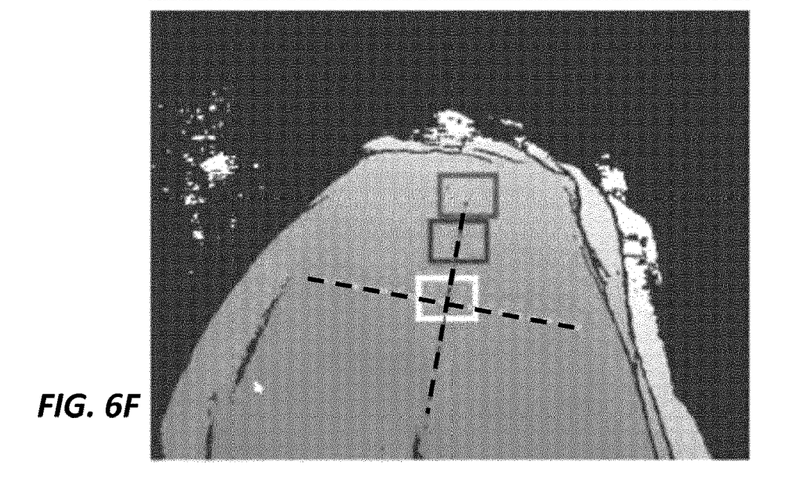
Figure 6G:
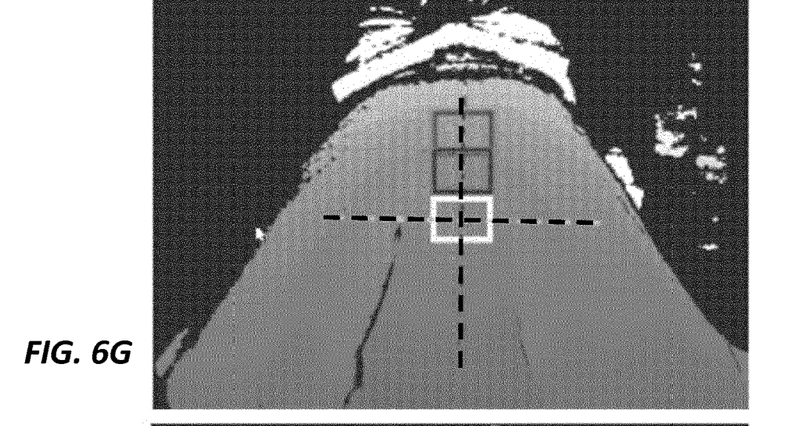
Figure 6H:
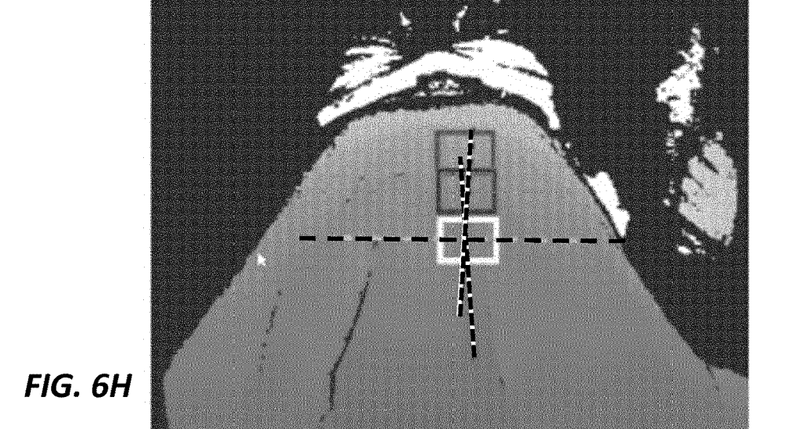
Figure 6I:
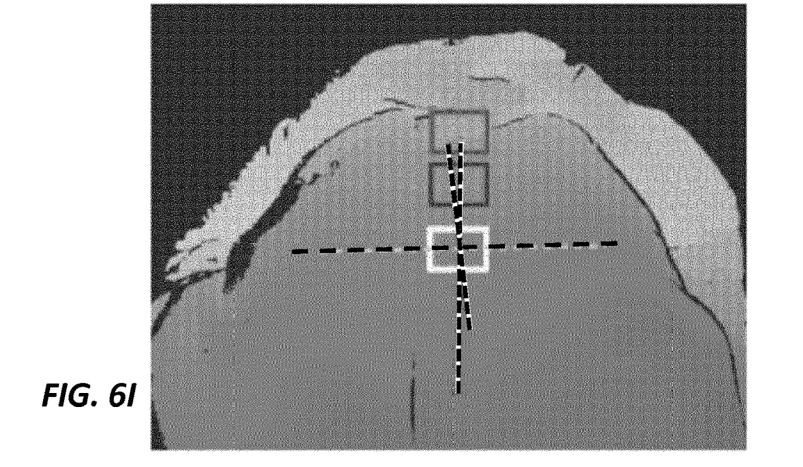

Regarding the measurement algorithm, a very low complexity and fast measurement algorithm has been implemented (as opposed to calibration where the geometric pose of the torso is determined), exemplified in FIGS. 5A-5C. The method involves computing the angle between the third principal component of the torso (from the calibrator) and the sensor, then the extraction of depth pixels in each measurement region, with averaging. Correction of the mean depth results in a true measure of breathing displacement, independent of viewing angle.

According to the current invention, tests have been carried out in a variety of scenarios, where, in the main use case with a vertical body position, the sensor is positioned at an angle relative to the torso, with a variation in the distance from the sensor to body, which is useful for different sized people, and angled torsos. In a further instance, both camera and patient movement were tested during calibration. Further, clutter in the field of view, including other people moving in the field of view were tested. Finally, different camera angles. The snapshots in FIGS. 6A-6I highlight the output of the markerless calibration system in a variety of situations, using both given and self-generated datasets.

The current invention provides the ability for dynamic calibration at real-time rates, and a method that is capable of handling a wider range of scenarios that include:

- optimizing parameters for a solution best satisfying the variety of scenarios that could be encountered
- algorithmic approaches to coping with different clothing types, coping with even more camera motion, handling extreme cases i.e. small children and large adults.
- reducing the number of thresholds and their respective sensitivities and tying these with a configuration file.
- measurement system optimizations for improved handling of local surface structure and data artifacts.
- calibration system improvements having sophisticated fitting for extending the operating characteristics, more robustness to clutter in the scene, etc.
- interfacing the breathing measurements to the breathing monitor system of the current invention, potentially with an automatic algorithm to select the best one based on e.g. harmonic purity (harmonics of a Fourier series corresponding to the breathing time series).

Regarding working with the camera intrinsics, the original depth image is converted to a point cloud by working with the IR camera intrinsics, which is derived from camera factory calibration, resulting in a 3×3 matrix K.

Working with the inverse Kinv, provides, in the code:

The matrix K and Kinv is flattened into a [1×9] vector for convenience (index K0,0 K0,1 K0,2 K1,0 K1,1 K1,2 K2,0 K2,1 K2,2 respectively). To compute K:

K[0]=depth Focal Length Pixels (x)
K[1]=0;
K[2]=depth Principal Point (x)
K[3]=0;
K[4]=depth Focal Length Pixels y
K[5]=depth image height+1.0−depth Principal Point (y)
K[6]=0;
K[7]=0;
K[8]=1;

For each depth image value d in depth image at location x, y, the point cloud xp, yp, zp coordinates are the following:

$$xp=Kinv[0]*x+Kinv[1]+Kinv[2]$$

$$yp=Kinv[3]*x+Kinv[4]+Kinv[5]$$

$$zp=d$$

For cropping along the z-direction, the invention uses the following method, the following configurable parameters include:

```
"Thresholds": {
    "fitter_residual_threshold": 0.05,
    "threshold_torso_z_m": 0.15,
    "threshold_torso_horizontal_m": 0.15,
    "torso_mesh_resolution_m": 0.005,
    "threshold_torso_yaxis_head": 0.2,
    "threshold_torso_yaxis_stomach": −0.25,
    "numits": 100
}
```

For the z-cropping, these are hardcoded in the code:
Minimum z: z_min_m=220.0/1000.0;
Maximum z: z_max_m=1200.0/1000.0;
Note also the "threshold_torso_z_m" parameter controls the maximum vertical distance (i.e. chest to back)

For the covariance matrix computation from the point cloud, a SelfAdjointEigenSolver is used that includes Main steps, where Eigen library notation is used here:

First the point cloud is normalized—the mean point cloud x,y,z value is subtracted:

centres=mat2.colwise( ).mean( );

centered=mat2.rowwise( )−centres.transpose( );

Covariance is computed fast using:

Eigen::MatrixXd cov=(centered.adjoint( )*centered)/double(numrows−1);

For determining the center of the point cloud for use as the anchor, the first workflow uses the mean (x, y, z) value of the point cloud. The second workflow is far superior here—point cloud vertices belonging to the torso are first isolated, which is to distinguished data from other clutter that shifts the mean e.g. people standing next to the bed, or the bed itself.

Given a point cloud P comprising N vertices the process includes identifing a subset of vertices Pf with Nf vertices (Nf<=N) where the vertices "fit" to a torso model, defined as a quadratic surface, then computing the mean (x, y, z) coordinates of Pf.

Regarding the second-order quadratic and linear (4-parameter) model implementation with the point cloud to form the 3-D curved surface for reducing clutter from clothing and body shape, the following method is used that is robust to the noise, missing data and non-randomly sampled point cloud, which includes using the robust RANSAC statistical fitter methodology. The algorithm involves randomly sampling points from the point cloud, with N points each time—N is 4 in the case for a model with 4 parameters. Two main methods are used:

1. FitFunctionQuadraticSurface3D—to fit this equation: $z=a\ x^2+b\ x+c\ y+d$.
2. ComputeResidualQuadraticSurface3D—Compute error residual between quadratic surface and a test pont $z=a\ x^2+bx+cy+d$ The algorithm relies on the curved surface to occupy a large part of the point cloud. The second step removes points from external clutter if they do not fit the model well. The algorithm is controlled by these two parameters:

"fitter_residual_threshold": 0.05, i.e. maximum residual error for a point to be considered to lie on the fitted surface "numits": 100 i.e. number of RANSAC iterations The purpose of the fitter-pca method is a series of steps to cope with high statistical variability, noise and sampling artifacts. Most importantly the method allows one to firstly find the torso (fitter), and secondly determine orientation (PCA). The various constraints are applied as the algorithm progresses, but note that an underlying constraint is computational complexity, where the purpose is to reduce the size of the data early on (cropping upfront) then filtering out after torso fit, leaving the computation with less data to process, where applying constraints at the end is slower. Once the torso is identified, this data is used as a rough basis to remove non-torso data on an anatomical basis.

According to one aspect of the invention data is removed symmetrically along the vertical axis of the torso to enforce the vertically elongated filtered point cloud, resulting an accurate principal direction in the final stage. This implementation increases the robustness in scenarios where the field of view is not ideal e.g. when a very large person is lying down, where the main torso direction is more difficult to estimate.

Figure 4A:
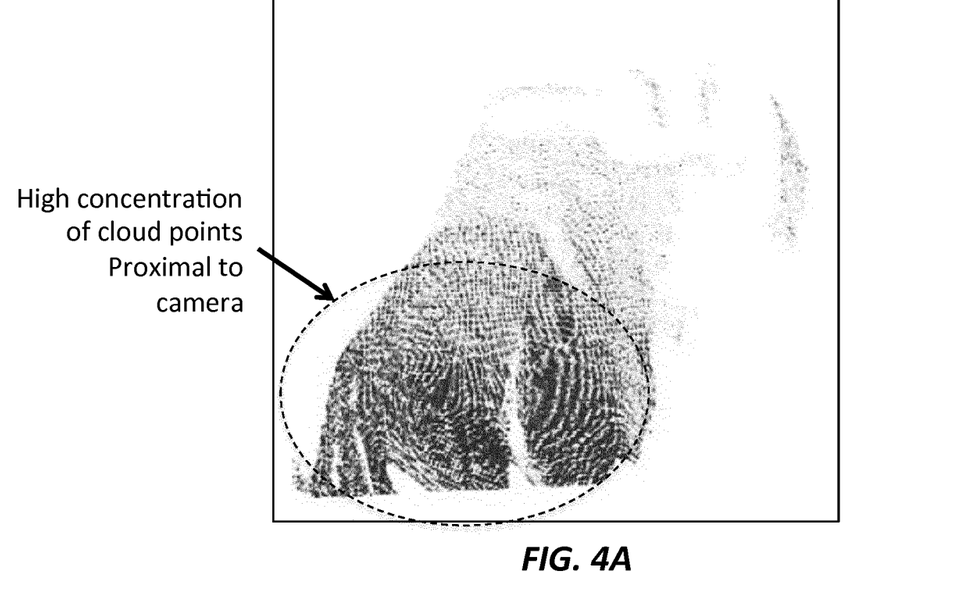
FIGS. 4A-4B show range torso point cloud (4A) illustrating dense sampling on the top of the torso (close to a projector such as IR, 3D camera) compared to the bottom, (4B) the point cloud has been uniformly sampled across the torso 3D model, thus removing the sample bias, according to the current invention.
Figure 4B:
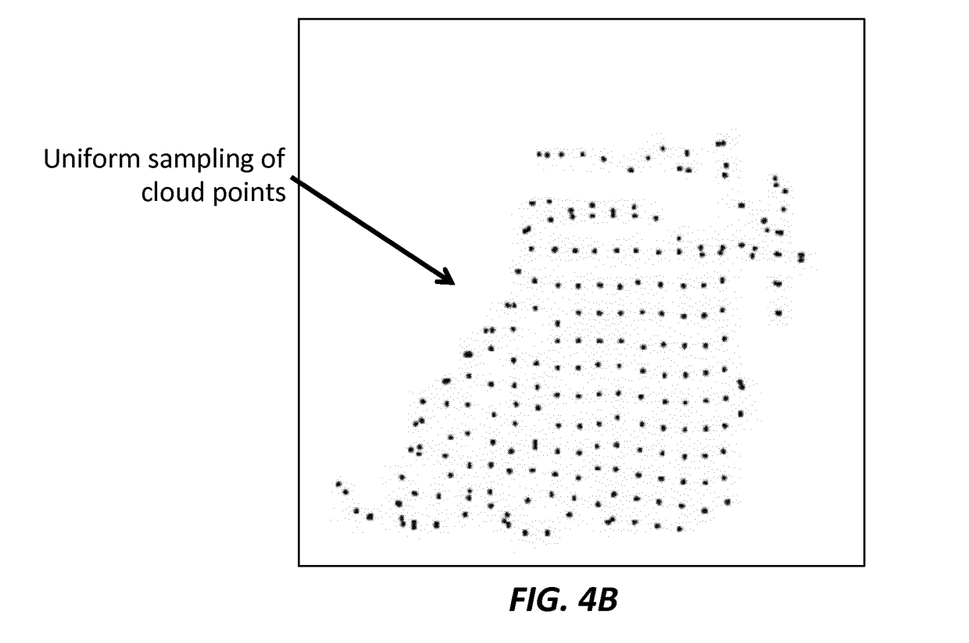

As shown in FIGS. 4A-4B, for mesh resampling to identify criteria for the uniformly sampled point cloud, a resampler makes use of the torso model to determine how to resample the mesh. This is a subtle but essential part of the method, where for this type of sensor and geometry (large perspective differences between the top and bottom of the torso), objects close to the camera are sampled a lot compared to further away ones. This is sub-optimal for statistical algorithms like PCA that inherently assume uniform sampling. As such, the fitter itself is the original enabler.

Main steps (implementation include
Remaining data is assumed to lie on a $z=a\ x^2+b\ x+c\ y+d$ surface
Create a uniformly sampled mesh centered on the position of our fitted torso polygon, and apply spatial constraints shown earlier—here the knowledge of the physical embodimen, and basic physiological limits are used. After choosing a mesh resolution, the width and height of the mesh is determined from the domain of the fitted data (i.e. a bounding box around the x-y locations of the fitted data. Here, the algorithm includes:
width and height of mesh:

$w\_mesh=2*\_thresholds.threshold\_torso\_horizontal\_m/thresholds.torso\_mesh\_resolution\_m;$ $h\_mesh=(\_thresholds.threshold\_torso\_yaxis\_head-\_thresholds.threshold\_torso\_yaxis\_stomach)/\_thresholds.torso\_mesh\_resolution\_m;$ bounding region for mesh $x\_mesh\_min=centreX-\_thresholds.threshold\_torso\_horizontal\_m;$ $x\_mesh\_max=centreX+\_thresholds.threshold\_torso\_horizontal\_m;$ $y\_mesh\_min=centreY+thresholds.threshold\_torso\_yaxis\_stomach;$ $y\_mesh\_max=centreY+thresholds.threshold\_torso\_yaxis\_head;$ After this, the method loops through each mesh element with the filtered point cloud, and specifies whether there exists data therein or not. An additional criteria used is to subtract the fit residual at each step from the "crest" of the surface (where the torso centre line is expected to be) i.e. where x=0 for $z=a\ x^2+bx+cy+d \rightarrow$ that is $z'=c\ y+d$. This results in a uniformly sampled mesh, which excludes regions without data present.

It is important to note that this new uniformly sampled mesh is then used to compute PCA on it, where the point cloud is first taken, then the torso fitter is applied, followed by the uniformly resample mesh, and then the PCA is run. The uniform resampling makes sure PCA is not biased towards the closer part of the torso.

The present invention has now been described in accordance with several exemplary embodiments, which are intended to be illustrative in all aspects, rather than restrictive. Thus, the present invention is capable of many variations in detailed implementation, which may be derived from the description contained herein by a person of ordinary skill in the art. All such variations are considered to be within the scope and spirit of the present invention as defined by the following claims and their legal equivalents.

What is claimed:

1. A method of real-time markerless measurement and calibration of a patient positioning system (PCA), comprising:

a) using a computer to compute a three dimensional point cloud representation of a patient by using a camera to obtain a plurality of depth points (X, Y, z) of said patient, wherein said camera comprises pixel coordinates (x, y) and depth to target z, wherein said X-direction corresponds to a lateral dimension of said patient, where said Y-direction corresponds to a longitudinal direction of said patient, wherein said z-direction corresponds to a direction along a focal length of said camera, wherein for each said (x, y) and said (X, Y, z) a corresponding point cloud coordinate xp, yp, z is determined as a function of said camera focal length, camera sensor center position, pixel size and lens distortion parameters;

b) demanding a z-limit on said Z-direction that corresponds to a lower (z-min) and an upper (z-max) specification;

c) computing a point cloud covariance and a point cloud mean, wherein said covariance and said mean of said point cloud are used to perform an optimized principle components analysis, wherein said principle components are determined;

d) sorting said principle components according to their maximum eigen-values, wherein said sorted principle components are used to compute a torso topography of said patient;

e) determining a center point of said point cloud, wherein said center point is used as an anchor measurement region of said patient, wherein a plurality of other measurement regions are determined along the Y-direction of said patient, wherein an eigen-vector of least variance along said z-direction is determined from all said measurement regions, wherein said least variance eigen-vector is perpendicular to said patient;

f) using said camera to determine a distance to said patient along said least variance eigen-vector in real-time; and g) outputting a real-time patient torso position, wherein said least variance eigen-vector of said anchor measurement region establishes an angle between a patient torso and a vector that is perpendicular to said camera, wherein a difference in displacement of said patient torso is computed by averaging the depth measurements in the reference regions and compensating for a parallax error in real-time during a calibration measurement or during a radiotherapy treatment plan.

2. The method according to claim 1, wherein after demanding said z-limit a torso fitter is applied, wherein said torso fitter comprises removing non-torso data of said patient.

3. The method according to claim 2, wherein after applying said torso fitter, body metric constraints are applied to said patient, wherein said body constraints and said measurement regions are used to remove data outside a threshold that is vertically below a surface of said patient, wherein a filtered point cloud is provided.

4. The method according to claim 3, wherein after applying said body metric constraints, said filtered point cloud is passed into a mesh resampling algorithm, wherein said mesh resampling algorithm demands an enhanced uniformity of a data sampling distribution across said torso of said patient, wherein said resampling algorithm reduces a data samples on said patient that are proximal to said camera and increases data samples on said patient that are distal to said patient, wherein an enhanced data uniformity is provided, wherein regions without data are excluded, wherein said enhanced data uniformity is used to compute said patient torso orientation by applying said torso fitter to said point cloud then uniformly resampling said mesh and repeating said real-time markerless measurement and calibration of a patient positioning process, wherein said uniform resampling makes sure said PCA is not biased towards a part of said patient torso that is proximal to said camera.

* * * * *